United States Patent [19]

Arndt et al.

[11] Patent Number: 5,461,161
[45] Date of Patent: Oct. 24, 1995

[54] N-PYRIDINYL[1,2,4]TRIAZOLO[1,5-C] PYRIMIDINE-2-SULFONAMIDE HERBICIDES

[75] Inventors: Kim E. Arndt; William A. Kleschick, both of Indianapolis, Ind.; Walter Reifschneider, Walnut Creek, Calif.; Robert J. Ehr, Indianapolis, Ind.

[73] Assignee: DowElanco, Indianapolis, Ind.

[21] Appl. No.: 273,514

[22] Filed: Jul. 11, 1994

[51] Int. Cl.⁶ .................................................. C07D 213/73
[52] U.S. Cl. ....................... 546/304; 504/241; 544/263; 546/297
[58] Field of Search .................. 544/263; 504/241; 546/297, 304

[56] References Cited

U.S. PATENT DOCUMENTS

| | | | |
|---|---|---|---|
| 3,926,611 | 12/1975 | Tomlin et al. | 546/304 |
| 4,638,075 | 1/1987 | Kleschick et al. | 544/263 |
| 4,818,273 | 4/1989 | Kleschick et al. | 544/263 |
| 4,886,883 | 12/1989 | Kleschick et al. | 544/263 |
| 4,976,946 | 11/1990 | King | 546/304 |
| 5,019,565 | 5/1991 | Baker et al. | 546/297 |
| 5,163,995 | 11/1992 | Van Heertum et al. | 544/263 |
| 5,201,938 | 4/1993 | Costales et al. | 544/263 |
| 5,300,478 | 4/1994 | Michaely et al. | 546/119 |

FOREIGN PATENT DOCUMENTS

| | | | |
|---|---|---|---|
| 244948 | 11/1987 | European Pat. Off. | 544/263 |
| 419831 | 8/1990 | European Pat. Off. . | |
| 3640155 | 5/1988 | Germany | 544/263 |

OTHER PUBLICATIONS

Hargrave et al., *Journal Medicinal Chemistry*, 34, 2231–2241 (1991).
Chapman et al., *Journal Chemical Society*, Perkin Trans. 1, 2398–2404 (1980).
Wieland et al., Annalen Chemie, 642, 163 (1961).

*Primary Examiner*—Donald G. Daus
*Attorney, Agent, or Firm*—D. Wendell Osborne

[57] ABSTRACT

Substituted N-pyridinyl[1,2,4]triazolo[1,5-c]-pyrimidine-2-sulfonamide compounds, such as N-(2-fluoro-4-methyl)-7-fluoro-5-methoxy[1,2,4]triazolo[1,5-c]pyrimidine-2-sulfonamide, were prepared by condensation of a 2-chlorosulfonyl[1,2,4]triazolo[1,5-c]pyrimidine compound, such as 2-chlorosulfonyl-7-fluoro-5-methoxy[1,2,4]triazolo[1,5-c]pyrimidine, with a substituted 3-aminopyridine compound, such as 3-amino-2-fluoro-4-methylpyridine, and found to possess herbicidal utility.

3 Claims, No Drawings

N-PYRIDINYL[1,2,4]TRIAZOLO[1,5-C] PYRIMIDINE-2-SULFONAMIDE HERBICIDES

BACKGROUND OF THE INVENTION

The present invention relates to substituted sulfonamide compounds, to herbicidal compositions containing the compounds, and to the utility of the compounds for the control of unwanted vegetation.

The control of unwanted vegetation by means of chemical agents, i.e., herbicides, is an important aspect of modern agriculture and land management. While many chemicals that are useful for the control of unwanted vegetation are known, new compounds that are more effective generally, are more effective for specific plant species, are less damaging to desirable vegetation, are safer to man or the environment, are less expensive to use, or have other advantageous attributes are desirable.

A number of sulfonamide compounds, including certain substituted [1,2,4]triazolo[1,5-a]pyrimidine-2-sulfonamide compounds (U.S. Pat. No. 4,954,163) and [1,2,4]triazolo[1,5-c]pyrimidine-2-sulfonamide compounds (U.S. Pat. No. 5,010,195 and European Application 244,948), are known and are known to possess herbicidal activity, especially on broadleaf weeds.

SUMMARY OF THE INVENTION

It has now been found that certain N-pyridinyl[1,2,4]triazolo[1,5-c]pyrimidine-2-sulfonamide compounds are potent herbicides for the control of unwanted vegetation, have desirable crop selectivity and have favorable toxicological and environmental attributes. The compounds are effective on grassy as well as broadleaf weeds.

The invention includes N-pyridinyl[1,2,4]triazolo[1,5-c]pyrimidine-2-sulfonamide compounds of Formula I:

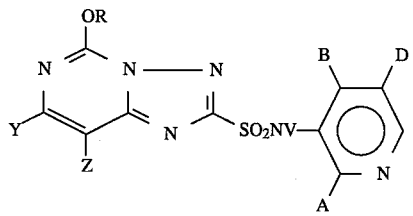

wherein

R represents $CH_2CF_3$ or $(C_1-C_3)$alkyl optionally monosubstituted with F, Cl, or $OCH_3$;

Y and Z each independently represents H, F, Cl, Br, I, $OCH_3$, $OC_2H_5$, $CH_3$ optionally mono to completely substituted with F;

V represents H, COR', $CO_2R''$, or $CONR'''_2$;

A and B each independently represents H, R', OR', $S(O)_nR'$, F, Cl, Br, I, CN, $NO_2$, $C_6H_5$, $CO_2R''$, or $CONR'''_2$ with the proviso that not more than one of A and B represents H;

D represents H, F, Cl, Br, I, $CF_3$, or $CH_3$;

n represents 0, 1, or 2;

R' represents $(C_1-C_4)$alkyl optionally singly to completely substituted with fluorine;

R" represents $(C_1-C_4)$alkyl, $(C_3-C_4)$alkenyl, or $(C_3-C_4)$alkynyl,

R'''' represents H or $(C_1-C_4)$ alkyl; and when V represents H, the agriculturally acceptable salts thereof.

The compounds of the invention, usually in the form of an herbicidal composition containing one or more of them in admixture with an agriculturally acceptable adjuvant or carrier, exhibit strong herbicidal properties when applied either directly to the unwanted vegetation or to the locus thereof and when applied either preemergence or postemergence.

DETAILED DESCRIPTION OF THE INVENTION

The N-pyridinyl [1,2,4]triazolo[1,5-c]pyrimidine- 2-sulfonamide compounds of the invention can be characterized as [1,2,4]triazolo[1,5-c]pyrimidine-2-sulfonamide compounds possessing an alkoxy substituent in the 5-position, alkyl, substituted alkyl, alkoxy, or halogen substituents in either or both of the 7- and 8-positions, and a substituted 3-pyridinyl moiety on the sulfonamide nitrogen atom. They are amides derived from a substituted [1,2,4]triazolo[1,5-c] pyrimidine-2-sulfonic acid compound and a substituted 3-aminopyridine compound.

The compounds of the invention include those of Formula I:

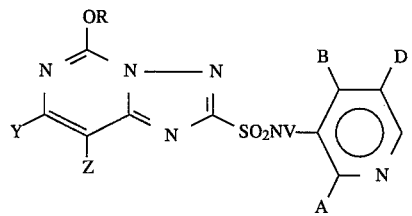

wherein R represents methyl, ethyl, propyl, 1-methylethyl, or cyclopropyl, each optionally monosubstituted with fluorine, chlorine or methoxy or represents 2,2,2-trifluoroethyl. Methyl and ethyl are typically preferred.

The Y and Z substituents of Formula I are independently selected and include hydrogen, methyl optionally mono to completely substituted with fluorine, or ethyl, fluoro, chloro, bromo, iodo, methoxy, or ethoxy. The substituents H, $CH_3$, F, Cl, and $OCH_3$ are typically preferred and compounds wherein one of Y and Z represents H, F, Cl, Br, I, $CH_3$, or $OCH_3$ and the other represents H are often more preferred.

The term V in Formula I generally represents hydrogen, $CO(C_1-C_4)$alkyl optionally singly to completely substituted with fluorine, $CO_2$ $(C_1-C_4)$alkyl, $CO_2$ $(C_3-C_4$ )alkenyl, $CO_2(C_3-C_4)$alkynyl, $CONH_2$, $CONH(C_1-C_4)$alkyl, or $CON((C_1-C_4)$alkyl$)_2$. Hydrogen is typically preferred.

Substituents A and B on the pyridine ring of the compounds of Formula I independently represent hydrogen, fluoro, chloro, bromo, iodo, cyano, nitro, phenyl, $CO_2(C_1-C_4)$alkyl, $CO_2(C_3-C_4)$alkenyl, or $CO_2(C_3-C_4)$alkynyl, $CONH_2$, $CONH(C_1-C_4)$alkyl, or $CON((C_1-C_4)$alkyl$)_2$, or represent $(C_1-C_4)$alkyl, $(C_1-C_4)$alkoxy, $(C_1-C_4)$alkylthio, (Cl-C4)alkylsulfinyl, or $(C_1-C_4)$alkylsulfonyl each optionally singly to completely substituted with fluorine, provided that at least one of A and B represents a substituent other than hydrogen. It is usually preferable that A and B both represent a substituent other than hydrogen. Methyl, ethyl, hydrogen, methoxy, ethoxy, propoxy, 1-methylethoxy, methoxycarbonyl, ethoxycarbonyl, fluoro, chloro, and bromo are often preferred substituents. The term D represents hydrogen, fluoro, chloro, bromo, iodo, trifluoromethyl, or methyl. It is often preferably hydrogen or methyl and is usually more preferably hydrogen. Compounds wherein A represents chloro, fluoro, or methoxy, B represents methyl, methoxy, ethoxy, propoxy, or 1-methylethoxy, and D represents hydrogen; or wherein A represents hydrogen, B represents methoxycarbonyl or ethoxycarbonyl, and D represents hydrogen are sometimes of special interest.

When V represents hydrogen, the compounds of Formula I are acidic and the invention includes the agriculturally acceptable salts.

The term alkyl as used herein includes straight chain, branched chain, and cyclic moieties. Thus, typical alkyl groups are methyl, ethyl, 1-methylethyl, propyl, cyclopropyl and the like. Methyl and ethyl are often preferred. Typical alkyl groups singly to completely substituted with fluorine include trifluoromethyl, monofluoromethyl, 2,2,2-trifluoroethyl, 2,3-difluoropropyl, and the like; trifluoromethyl is often preferred. Typical alkyl groups monosubstituted with methoxy or chloro include 2-chloroethyl, methoxymethyl, and 2-methoxy-1-methylethyl.

The term "agriculturally acceptable salts" is employed herein to denote compounds wherein the acidic sulfonamide proton of the compound of Formula I is replaced by a cation which itself is neither herbicidal to crop plants being treated nor significantly deleterious to the applicator, the environment, or the ultimate user of any crop being treated. Suitable cations include, for example, those derived from alkali or alkaline earth metals and those derived from ammonia and amines. Preferred cations include sodium, potassium, magnesium, and aminium cations of the formula:

$R^6R^7R^8NH^{\oplus}$ wherein $R^6$, $R^7$, and $R^8$ each, independently represents hydrogen or $(C_1-C_{12})$alkyl, $(C_3-C_{12})$cycloalkyl, or $(C_3-C_{12})$alkenyl, each of which is optionally substituted by one or more hydroxy, $(C_1-C_8)$alkoxy, $(C_1-C_8)$alkylthio or phenyl groups; provided that $R^6$, $R^7$, and $R^8$ are sterically compatible. Additionally, any two of $R^6$, $R^7$, and $R^8$ together may represent an aliphatic difunctional moiety containing 1 to 12 carbon atoms and up to two oxygen or sulfur atoms. Salts of the compounds of Formula I can be prepared by treatment of compounds of Formula I wherein V represents hydrogen with a metal hydroxide, such as sodium hydroxide, potassium hydroxide, or magnesium hydroxide, or an amine, such as ammonia, trimethylamine, hydroxyethylamine, bisallylamine, 2-butoxyethylamine, morpholine, cyclododecylamine, or benzylamine.

A listing of some typical compounds of the invention is given in Table 1. Some of the specifically preferred compounds of the invention include the following: N-(2-fluoro-4-methyl-3-pyridinyl)-5,8-dimethoxy[ 1,2,4]triazolo[1,5-c]pyrimidine-2-sulfonamide, N-(2-chloro-4-methoxy-3-pyridinyl)-5-methoxy-7-methyl[1,2,4]triazolo[1,5-c]pyrimidine-2-sulfonamide, N- (2-methoxy4-methyl-3-pyridinyl) -7-fluoro-5-methoxy[1,2,4]triazolo[1,5-c]pyrimidine-2-sulfonamide, N- (2-chloro-4-methoxy-3-pyridinyl)- 7-fluoro-5-methoxy[1,2,4]triazolo[1,5-c]pyrimidine-2-sulfonamide, N- (2-chloro -4-methyl -3-pyridinyl)-8-iodo-5-methoxy[1,2,4]triazolo[1,5-c]pyrimidine-2-sulfonamide, and N- (2-chloro-4-methoxy-3-pyridinyl) -7-chloro-5-ethoxy[1,2,4]triazolo[1,5-c]pyrimidine-2-sulfonamide.

TABLE 1

N-PYRIDINYL[1,2,4]TRIAZOLO[1,5-C]PYRIMIDINE-2-SULFONAMIDE COMPOUNDS

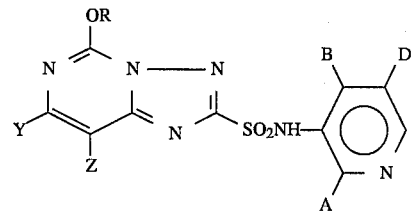

| Cpd. No. | R | Y | Z | A | B | D | Form | Melting point, °C. | % C calc. found | % H calc. found | % N calc. found | % S calc. found |
|---|---|---|---|---|---|---|---|---|---|---|---|---|
| 1 | $C_2H_5$ | H | $OCH_3$ | Cl | H | H | white powder | 225–226 | 40.6 40.3 | 3.41 3.61 | 21.8 21.5 | 8.33 8.12 |
| 2 | $C_2H_5$ | F | H | Cl | H | H | white crystals | 193–194 (d) | 38.6 38.7 | 2.70 2.69 | 22.5 22.4 | 8.60 8.73 |
| 3 | $CH_3$ | H | $OCH_3$ | $CO_2CH_3$ | H | H | white powder | 187–189 | 42.6 42.4 | 3.58 3.53 | 21.3 21.3 | 8.13 8.11 |
| 4 | $CH_3$ | H | I | Cl | H | H | solid | 197–200 (d) | 25.4 26.0 | 1.38 1.30 | 17.4 17.3 | 7.97 7.50 |
| 5 | $CH_3$ | H | I | $CO_2CH_3$ | H | H | pale yellow powder | 183–186 (d) | 31.9 32.2 | 2.26 2.28 | 17.1 17.2 | 6.54 6.79 |
| 6 | $C_2H_5$ | F | H | $CO_2CH_3$ | H | H | white powder | 182–183 | 42.4 42.4 | 3.31 3.35 | 21.2 21.2 | 8.09 7.94 |
| 7 | $CH_3$ | $CH_3$ | H | $CO_2CH_3$ | H | H | white powder | 181–182 | 44.4 44.7 | 3.72 3.68 | 22.2 22.5 | 8.47 8.12 |
| 8 | $CH_3$ | H | $OCH_3$ | H | $CO_2CH_3$ | H | dihydrate yellow powder | >300 (d) | 39.0 38.8 | 4.22 3.52 | 19.5 19.3 | 7.45 6.97 |
| 9 | $C_2H_5$ | F | H | H | $CO_2CH_3$ | H | white powder | 141–143 | 42.4 42.3 | 3.30 3.43 | 21.2 21.0 | 8.09 7.87 |
| 10 | $C_2H_5$ | F | H | Cl | $CO_2CH_3$ | H | tan powder | 191–192 (d) | 39.0 39.1 | 2.80 3.00 | 19.5 18.7 | 7.44 6.78 |
| 11 | $CH_3$ | H | $OCH_3$ | Cl | $CO_2CH_3$ | H | tan powder | 214–216 (d) | 39.2 39.5 | 3.06 2.97 | 19.6 19.7 | 7.48 7.28 |

TABLE 1-continued

N-PYRIDINYL[1,2,4]TRIAZOLO[1,5-C]PYRIMIDINE-2-SULFONAMIDE COMPOUNDS

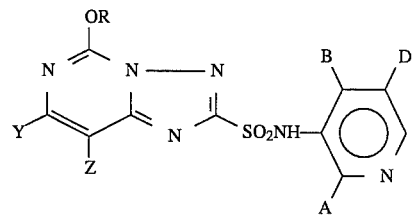

| Cpd. No. | R | Y | Z | A | B | D | Form | Melting point, °C. | % C calc. found | % H calc. found | % N calc. found | % S calc. found |
|---|---|---|---|---|---|---|---|---|---|---|---|---|
| 12 | CH₃ | H | I | Cl | CO₂CH₃ | H | white powder | 193–194 (d) | 29.8 / 30.2 | 1.92 / 1.83 | 16.0 / 16.2 | 6.11 / 6.06 |
| 13 | CH₃ | H | OCH₃ | Cl | CH₃ | H | off-white solid | 196–199 (d) | 40.5 / 40.6 | 3.40 / 3.62 | 21.8 / 21.9 | 8.32 / 8.11 |
| 14 | C₂H₅ | F | H | Cl | CH₃ | H | white solid | 177–179 (d) | 40.4 / 40.6 | 3.13 / 3.20 | 21.7 / 21.7 | 8.29 / 8.03 |
| 15 | CH₃ | H | OCH₃ | F | CH₃ | H | white powder | 217–218 (d) | 42.3 / 42.5 | 3.55 / 3.50 | 22.8 / 22.6 | 8.68 / 8.84 |
| 16 | CH₃ | H | I | Cl | CH₃ | H | white powder | 203–205 | 30.0 / 30.2 | 2.10 / 2.13 | 17.5 / 17.1 | 6.67 / 6.39 |
| 17 | CH₃ | H | CH₃ | Cl | CH₃ | H | pale yellow powder | 207–208 (d) | 42.3 / 42.2 | 3.55 / 3.40 | 22.8 / 22.5 | 8.69 / 8.42 |
| 18 | CH₃ | Cl | H | Cl | CH₃ | H | pale yellow powder | 193–194 (d) | 37.0 / 37.1 | 2.59 / 2.44 | 21.6 / 21.3 | 8.23 / 8.14 |
| 19 | CH₃ | H | Cl | Cl | CH₃ | H | white powder | 212–214 (d) | 37.0 / 37.2 | 2.59 / 2.46 | 21.6 / 21.6 | 8.23 / 8.01 |
| 20 | C₂H₅ | F | H | F | CH₃ | H | white powder | 188–189 (d) | 42.2 / 42.4 | 3.27 / 3.33 | 22.7 / 22.6 | 8.66 / 8.83 |
| 21 | CH₃ | CH₃ | H | Cl | CH₃ | H | white powder | 200–201 (d) | 42.3 / 42.4 | 3.55 / 3.42 | 22.8 / 22.5 | 8.69 / 8.79 |
| 22 | CH₃ | H | F | Cl | CH₃ | H | white powder | 203–204 (d) | 38.7 / 38.7 | 2.70 / 2.72 | 22.5 / 22.3 | 8.60 / 8.68 |
| 23 | CH₃ | H | H | Cl | CH₃ | H | white powder | 199–201 (d) | 40.6 / 40.6 | 3.13 / 3.12 | 23.7 / 23.5 | 9.04 / 8.78 |
| 24 | CH₃ | H | Cl | F | CH₃ | H | white powder | 204–205 (d) | 38.7 / 38.5 | 2.90 / 3.12 | 22.5 / 22.4 | 8.60 / 8.29 |
| 25 | CH₃ | Cl | H | F | CH₃ | H | white powder | 182–183 (d) | 38.7 / 38.6 | 2.90 / 2.70 | 22.5 / 22.3 | 8.60 / 8.49 |
| 26 | CH₃ | H | F | F | CH₃ | H | tan powder | 190–192 (d) | 40.4 / 40.4 | 2.83 / 3.15 | 22.5 / 22.3 | 8.60 / 8.49 |
| 27 | CH₃ | CH₃ | H | F | CH₃ | H | white powder | 194–195 (d) | 44.3 / 44.4 | 3.72 / 3.74 | 23.9 / 24.1 | 9.10 / 9.27 |
| 28 | CH₃ | H | OCH₃ | Cl | OCH₃ | H | white powder | 196–197 (d) | 39.0 / 39.2 | 3.27 / 3.34 | 21.0 / 20.8 | 8.00 / 7.90 |
| 29 | CH₃ | H | I | F | CH₃ | H | white powder | 194–196 (d) | 30.9 / 31.0 | 2.16 / 2.36 | 18.0 / 18.0 | 6.86 / 6.60 |
| 30 | C₂H₅ | F | H | Cl | OCH₃ | H | white powder | 176–178 (d) | 38.8 / 38.6 | 3.00 / 2.95 | 20.9 / 20.8 | 7.96 / 7.90 |
| 31 | CH₃ | H | OCH₃ | Cl | Cl | H | white powder | 215–216 (d) | 35.6 / 35.6 | 2.49 / 2.75 | 20.7 / 20.5 | 7.91 / 7.62 |
| 32 | C₂H₅ | F | H | Cl | Cl | H | white powder | 196–197 (d) | 35.4 / 35.6 | 2.23 / 2.61 | 20.6 / 20.3 | 7.87 / 7.45 |
| 33 | CH₃ | H | CH₃ | F | CH₃ | H | white powder | 206–207 (d) | 44.3 / 44.5 | 3.72 / 3.58 | 23.9 / 24.1 | 9.10 / 9.38 |
| 34 | CH₃ | H | H | F | CH₃ | H | white powder | 194–195 (d) | 42.6 / 42.6 | 3.28 / 3.39 | 24.8 / 24.8 | 9.48 / 9.83 |
| 35 | CH₃ | CH₃ | H | Cl | OCH₃ | H | white solid | 195–196 (d) | 40.6 / 40.8 | 3.41 / 3.59 | 21.8 / 21.7 | 8.33 / 8.08 |
| 36 | CH₃ | F | H | OCH₃ | CH₃ | H | white powder | 177–178 (d) | 42.4 / 42.3 | 3.56 / 3.64 | 22.4 / 22.8 | 8.70 / 7.92 |
| 37 | CH₃ | H | OCH₃ | OCH₃ | CH₃ | H | white powder | 192–193 (d) | 44.2 / 44.2 | 4.24 / 4.41 | 22.1 / 22.4 | 8.43 / 8.43 |
| 38 | CH₃ | F | H | Cl | CH₃ | H | white powder | 170–175 (d) | 38.7 / 38.8 | 2.70 / 2.76 | 22.6 / 21.3 | 8.60 / 7.93 |
| 39 | CH₃ | H | I | OCH₃ | CH₃ | H | white powder | 195–197 (d) | 32.8 / 33.1 | 2.75 / 2.67 | 17.7 / 17.4 | 6.73 / 6.78 |
| 40 | CH₃ | H | OCH₃ | Br | CH₃ | H | tan powder | 187–190 (d) | 36.4 / 36.7 | 3.05 / 3.18 | 19.6 / 19.4 | 7.47 / 7.83 |
| 41 | CH₃ | F | H | Br | CH₃ | H | white powder | 180–182 (d) | 34.6 / 34.7 | 2.42 / 2.57 | 20.1 / 20.1 | 7.68 / 7.82 |
| 42 | CH₃ | CH₃ | H | Br | CH₃ | H | white powder | 183–185 (d) | 37.8 / 38.0 | 3.17 / 3.56 | 20.3 / 19.9 | 7.76 / 8.05 |

TABLE 1-continued

N-PYRIDINYL[1,2,4]TRIAZOLO[1,5-C]PYRIMIDINE-2-SULFONAMIDE COMPOUNDS

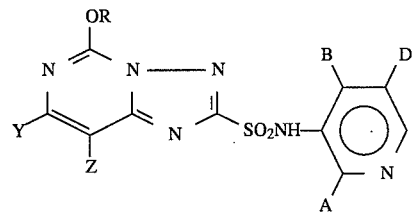

| Cpd. No. | R | Y | Z | A | B | D | Form | Melting point, °C. | % C calc. found | % H calc. found | % N calc. found | % S calc. found |
|---|---|---|---|---|---|---|---|---|---|---|---|---|
| 43 | CH₃ | H | OCH₃ | SC₂H₅ | CH₃ | H | light yellow powder | 176–178 (d) | 43.9 43.7 | 4.42 4.51 | 20.5 20.0 | 15.6 14.9 |
| 44 | CH₃ | F | H | SC₂H₅ | CH₃ | H | light gray powder | 170–172 (d) | 42.2 42.5 | 3.79 3.94 | 21.1 20.9 | 16.1 15.8 |
| 45 | CH₃ | F | H | F | CH₃ | H | white powder | 190–192 | 40.5 40.5 | 2.83 2.53 | 23.6 23.5 | 9.00 9.09 |
| 46 | CH₃ | OCH₃ | H | F | CH₃ | H | white powder | 204–205 (d) | 42.4 42.3 | 3.56 3.67 | 22.8 22.6 | 8.70 8.94 |
| 47 | CH₃ | Cl | H | Cl | OCH₃ | H | white powder | 183–185 (d) | 35.6 35.6 | 2.49 2.31 | 20.7 20.4 | 7.91 7.92 |
| 48 | CH₃ | H | Cl | Cl | CH₃ | H | white powder | 194–195 (d) | 35.6 35.7 | 2.49 2.38 | 20.7 20.5 | 7.91 7.89 |
| 49 | C₂H₅ | Cl | H | Cl | CH₃ | H | tan powder | 188–189 (d) | 38.7 38.8 | 3.00 2.93 | 20.8 20.7 | 7.95 7.94 |
| 50 | C₂H₅ | Cl | H | F | CH₃ | H | tan powder | 195–196 (d) | 40.4 40.5 | 3.13 3.04 | 21.7 21.7 | 8.29 8.53 |
| 51 | C₂H₅ | CH₃ | H | Cl | OCH₃ | H | white solid | 194–195 | 42.2 42.4 | 3.79 4.02 | 21.1 19.9 | 8.04 8.03 |
| 52 | CH₃ | H | Br | F | CH₃ | H | tan powder | 189–191 (d) | 34.6 34.9 | 2.42 2.83 | 20.1 19.9 | 7.68 7.96 |
| 53 | C₂H₅ | CH₃ | H | F | CH₃ | H | white powder | 210–211 (d) | 45.9 46.1 | 4.13 4.17 | 22.9 23.1 | 8.75 8.94 |
| 54 | C₂H₅ | H | F | F | CH₃ | H | white powder | 204–205 (d) | 42.2 42.2 | 3.27 2.87 | 22.7 22.4 | 8.66 8.77 |
| 55 | C₂H₅ | H | F | Cl | CH₃ | H | white powder | 216–217 (d) | 40.4 40.5 | 3.13 2.97 | 21.7 21.7 | 8.29 8.11 |
| 56 | C₂H₅ | H | F | Cl | OCH₃ | H | white powder | 205–207 (d) | 38.8 39.0 | 3.00 2.96 | 20.9 20.8 | 7.96 8.06 |
| 57 | CH₃ | F | H | Cl | OCH₃ | H | white powder | 187–189 (d) | 37.1 37.3 | 2.59 2.46 | 21.6 21.5 | 8.25 8.22 |
| 58 | CH₃ | OCH₃ | H | Cl | OCH₃ | H | tan solid | 197–199 (d) | 39.0 38.9 | 3.27 3.40 | 21.0 20.9 | |
| 59 | CH₃ | H | CH₃ | Cl | OCH₃ | H | tan solid | 197–198 (d) | 40.6 40.4 | 3.41 3.42 | 21.8 21.1 | |
| 60 | CH₃ | CH₂—OCH₃ | H | F | CH₃ | H | white powder | 199–200 (d) | 44.0 43.9 | 3.95 3.92 | 22.0 21.8 | 8.38 8.50 |
| 61 | CH₃ | H | F | Cl | OCH₃ | H | white powder | 185–190 (d) | 37.1 37.1 | 2.59 2.38 | 21.6 21.4 | 8.25 8.25 |
| 62 | CH₃ | SCH₃ | H | Cl | OCH₃ | H | white powder | 185–186 (d) | 37.5 37.5 | 3.14 3.26 | 20.2 20.2 | 15.4 15.2 |
| 63 | C₂H₅ | Cl | H | Cl | OCH₃ | H | white powder | 183–184 (d) | 37.2 37.5 | 2.89 2.72 | 20.0 19.8 | 7.65 7.88 |
| 64 | CH₃ | F | H | F | H | CH₃ | white powder | 178–179 (d) | 40.5 40.3 | 2.83 2.93 | 23.6 23.4 | 9.00 9.25 |
| 65 | CH₃ | CH₃ | H | F | CH₃ | H | white powder | 191–192 (d) | 44.3 44.2 | 3.72 3.82 | 23.9 23.9 | 9.10 9.36 |
| 66 | CH₃ | H | OCH₃ | F | H | CH₃ | white solid | 174–176 (d) | | | | |
| 67 | CH₃ | H | OCH₃ | H | CF₃ | H | light yellow solid | 221–222 | 38.6 38.5 | 2.74 2.63 | 20.8 20.5 | 7.93 7.76 |
| 68 | CH₃ | CH₃ | H | H | CF₃ | H | white powder | 193–194 | 40.2 40.0 | 2.86 2.66 | 21.6 21.7 | 8.26 8.43 |
| 69 | CH₃ | CH₃ | H | H | CO₂CH₃ | H | white powder | 156–157 | 44.4 44.6 | 3.73 3.59 | 22.2 22.1 | 8.47 8.58 |
| 70 | C₂H₅ | F | H | F | H | Cl | tan powder | 193–194 (d) | 36.9 37.1 | 2.32 2.43 | 21.5 21.4 | 8.20 7.98 |
| 71 | CH₃ | CH₃ | H | F | H | Cl | white powder | 205–206 (d) | 38.7 38.5 | 2.70 2.57 | 22.6 22.5 | 8.60 8.60 |
| 72 | C₂H₄Cl | CH₃ | H | F | CH₃ | H | tan powder | 180–184 | | | | |
| 73 | CH₂CF₃ | CH₃ | H | F | CH₃ | H | white powder | 215–218 | 40.0 40.1 | 2.88 2.66 | 20.0 19.8 | 7.63 7.45 |

TABLE 1-continued

N-PYRIDINYL[1,2,4]TRIAZOLO[1,5-C]PYRIMIDINE-2-SULFONAMIDE COMPOUNDS

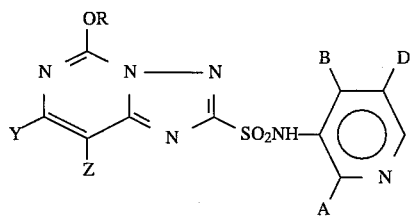

| Cpd. No. | R | Y | Z | A | B | D | Form | Melting point, °C. | % C calc. found | % H calc. found | % N calc. found | % S calc. found |
|---|---|---|---|---|---|---|---|---|---|---|---|---|
| 74 | CH₃ | CH₃ | H | H | CH₃ | H | white solid | 188–190 | 46.7 46.8 | 4.22 4.06 | 25.1 24.9 | 9.59 9.87 |
| 75 | C₂H₅ | CH₃ | H | H | CO₂CH₃ | H | white powder | 180–181 | 45.9 46.2 | 4.11 4.01 | 21.4 21.6 | 8.17 8.34 |
| 76 | C₂H₅ | F | H | H | CH₃ | H | white powder | 161–163 | 44.3 44.4 | 3.72 4.09 | 23.9 23.6 | 9.10 8.93 |
| 77 | CH₃ | F | OCH₃ | F | CH₃ | H | tan solid | 177–180 | 40.4 40.7 | 3.13 3.61 | 21.8 21.1 | 8.30 8.05 |
| 78 | CH₃ | CH₃ | H | OCH₃ | CH₃ | H | white solid | 215–216 | 46.2 46.3 | 4.43 4.56 | 23.1 23.2 | 8.80 8.36 |
| 79 | CH₃ | CH₃ | H | H | CO₂C₂H₅ | H | white solid | 152–153 | 45.9 45.5 | 4.12 4.24 | 21.4 21.5 | 8.17 8.12 |
| 80 | CH₃ | CH₃ | H | Cl | Cl | H | white solid | 195–196 (d) | 37.0 40.8 | 2.59 3.13 | 21.6 21.8 | 8.24 7.76 |
| 81 | CH₃ | CH₃ | H | Cl | C₂H₅ | H | white solid | 202–203 | 42.2 42.4 | 3.79 3.38 | 21.1 21.1 | 8.04 7.72 |
| 82 | CH₃ | F | H | Cl | C₂H₅ | H | white solid | 156–157 | 40.3 40.4 | 3.39 3.65 | 20.2 20.0 | 7.69 7.78 |
| 83 | CH₃ | CH₃ | H | H | CO₂—C₃H₇(i) | H | white solid | 158–159 | 47.3 47.5 | 4.46 4.84 | 20.7 20.7 | 7.89 7.46 |
| 84 | CH₃ | CH₃ | H | H | C₂H₅ | H | white solid | 184–186 | 46.2 46.5 | 4.43 4.37 | 23.1 22.8 | 8.08 7.98 |
| 85 | C₂H₅ | F | H | H | CO₂—C₃H₇(i) | H | white solid | 168–169 | 45.3 45.5 | 4.04 4.20 | 19.8 19.6 | 7.55 7.48 |
| 86 | CH₃ | CH₃ | H | H | Cl | H | white solid | 218–223 (d) | 47.3 47.5 | 3.64 3.50 | 20.3 20.1 | 7.73 7.43 |
| 87 | CH₃ | H | OCH₃ | F | C₂H₅ | H | white solid | 191–192 (d) | 44.0 43.8 | 3.95 3.73 | 22.0 22.0 | 8.38 8.57 |
| 88 | C₂H₅ | F | H | F | C₂H₅ | H | white solid | 192–193 (d) | 43.8 43.8 | 3.67 3.57 | 21.9 21.8 | 8.34 8.57 |
| 89 | CH₃ | CH₃ | H | F | C₂H₅ | H | white solid | 208–209 | 45.9 45.7 | 4.13 4.40 | 22.9 22.8 | 8.76 8.76 |
| 90 | CH₃ | CH₃ | H | Cl | OC₃H₇(n) | H | white solid | 175–176 | 43.6 44.0 | 4.15 4.20 | 20.3 20.4 | 7.77 7.45 |
| 91 | CH₃ | CH₃ | H | Cl | OC₃H₇(i) | H | white solid | 199–200 | 43.6 43.5 | 4.15 4.11 | 20.4 20.5 | 7.77 7.39 |
| 92 | C₂H₅ | F | H | Cl | OC₃H₇(n) | H | tan solid | 159–160 (d) | 41.8 41.9 | 3.74 3.83 | 19.5 19.4 | 7.44 7.72 |
| 93 | C₂H₅ | F | H | Cl | OC₃H₇(i) | H | white solid | 181–182 (d) | 41.8 41.6 | 3.74 3.96 | 19.5 18.9 | 7.44 7.58 |
| 94 | CH₃ | CH₃ | H | F | C₃H₇(i) | H | white solid | 199–200 (d) | 47.4 47.4 | 4.50 4.61 | 22.1 21.9 | 8.43 8.32 |
| 95 | CH₃ | F | H | Cl | OC₃H₇(i) | H | white solid | 209–211 (d) | 40.3 39.9 | 3.39 3.57 | 20.2 19.9 | 7.69 7.42 |
| 96 | C₂H₅ | CH₃ | H | F | OC₃H₇(i) | H | white solid | 212–213 (d) | 45.0 44.9 | 4.49 4.40 | 19.7 19.5 | 7.51 6.65 |
| 97 | C₂H₅ | F | H | Cl | Cl | Cl | white solid | 218–219 (d) | 32.6 33.0 | 1.83 1.96 | 19.0 19.1 | 7.26 7.14 |
| 98 | CH₃ | CH₃ | H | Cl | Cl | Cl | white solid | 200–202 (d) | 34.0 34.3 | 2.14 1.91 | 19.8 19.7 | 7.57 7.43 |
| 99 | CH₃ | H | Br | Cl | C₂H₅ | H | white solid | 174–175 (d) | 33.7 33.8 | 2.61 2.67 | 18.1 17.9 | 6.91 7.03 |
| 100 | CH₃ | H | Br | Cl | OCH₃ | H | white solid | 194–197 (d) | 32.1 32.2 | 2.24 2.30 | 18.7 18.8 | 7.13 7.00 |
| 101 | C₂H₅ | CH₃ | H | Cl | C₂H₅ | H | white solid | 196–198 (d) | 43.6 43.6 | 4.15 4.26 | 20.4 20.2 | 7.77 7.92 |
| 102 | CH₃ | H | I | Cl | C₂H₅ | H | tan solid | 184–185 (d) | 30.6 30.7 | 2.37 2.39 | 16.5 16.0 | 6.28 5.46 |
| 103 | CH₃ | H | Cl | Cl | C₂H₅ | H | yellow solid | 172–173 (d) | 37.2 37.4 | 2.89 3.06 | 20.1 19.7 | 7.65 7.01 |
| 104 | C₂H₅ | CH₃ | H | Cl | OC₃H₇(n) | H | yellow solid | 165–167 (d) | 45.0 44.9 | 4.49 4.51 | 19.7 19.3 | 7.51 7.21 |

TABLE 1-continued
N-PYRIDINYL[1,2,4]TRIAZOLO[1,5-C]PYRIMIDINE-2-SULFONAMIDE COMPOUNDS

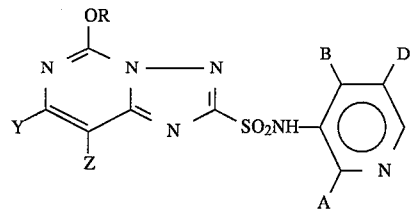

| Cpd. No. | R | Y | Z | A | B | D | Form | Melting point, °C. | % C calc. found | % H calc. found | % N calc. found | % S calc. found |
|---|---|---|---|---|---|---|---|---|---|---|---|---|
| 105 | CH₃ | CH₃ | H | Cl | CO₂CH₃ | H | white solid | 206–208 (d) | 40.7 40.6 | 3.17 3.05 | 20.4 20.2 | 7.77 7.69 |
| 106 | CH₃ | C₃H₇(i) | H | F | CH₃ | H | orange solid | 160–162 | 47.4 47.9 | 4.50 4.26 | 22.1 20.1 | 8.43 7.56 |
| 107 | C₃H₇(i) | CH₃ | H | Cl | OCH₃ | H | colorless solid | 202–203 (d) | 43.6 43.4 | 4.15 4.18 | 20.4 20.1 | 7.77 7.58 |
| 108 | C₃H₇(i) | CH₃ | H | F | CH₃ | H | tan solid | 198–199 (d) | 47.4 47.4 | 4.50 4.39 | 22.1 21.4 | 8.43 7.67 |
| 109 | C₃H₇(i) | CH₃ | H | Cl | OC₂H₅ | H | yellow solid | 168–170 | 45.0 45.2 | 4.49 4.79 | 19.7 19.4 | 7.51 7.40 |
| 110 | CH₃ | CH₃ | H | F | OCH₃ | H | | | | | | |
| 111 | CH₃ | CH₃ | H | Br | OCH₃ | H | | | | | | |
| 112 | C₂H₅ | F | H | F | OCH₃ | H | | | | | | |
| 113 | C₂H₅ | F | H | Br | OCH₃ | H | | | | | | |
| 114 | C₂H₅ | F | H | F | OC₂CH₃ | H | | | | | | |
| 115 | C₂H₅ | F | H | OCH₃ | Cl | H | | | | | | |
| 116 | C₂H₅ | F | H | OCH₃ | CO₂CH₃ | H | | | | | | |
| 117 | C₂H₅ | F | H | Cl | OCH₂CF₃ | H | | | | | | |
| 118 | C₂H₅ | F | H | F | I | H | | | | | | |
| 119 | C₂H₅ | F | H | OC₂H₅ | CH₃ | H | | | | | | |
| 120 | C₂H₅ | F | H | F | CO₂CH₃ | H | | | | | | |
| 121 | CH₃ | CH₃ | H | OCH₃ | Cl | H | | | | | | |
| 122 | CH₃ | CH₃ | H | OCH₃ | CO₂CH₃ | H | | | | | | |
| 123 | CH₃ | CH₃ | H | Cl | OCH₂CF₃ | H | | | | | | |
| 124 | CH₃ | CH₃ | H | F | I | H | | | | | | |
| 125 | CH₃ | CH₃ | H | OC₂H₅ | CH₃ | H | | | | | | |
| 126 | CH₃ | CH₃ | H | Cl | OCH₃ | Cl | | | | | | |
| 127 | CH₃ | CH₃ | H | F | CO₂CH₃ | H | | | | | | |

The compounds of Formula I wherein V represents hydrogen can generally be prepared by combining a 2-chlorosulfonyl[1,2,4]triazolo[1,5-c]pyridine compound of Formula II:

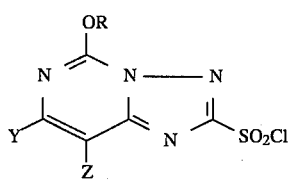

with an appropriately substituted aminopyridine compound of Formula III:

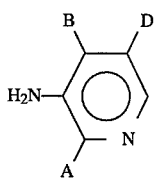

in the presence of pyridine or a methylpyridine compound, and, optionally but preferably, a catalytic amount of dimethyl sulfoxide. The substituents OR, Y, and Z of Formula II and A, B, and D of Formulas III are as defined hereinbefore.

The preparation is usually accomplished by combining the 2-chlorosulfonyl[1,2,4]triazolo[1,5-c]pyrimidine compound Formula II, the aminopyridine of Formula III, and an inert solvent, such as acetonitrile, N,N-dimethylformamide, N-methyl2-pyrrolidinone, tetrahydrofuran, and the like, in a vessel and then adding the pyridine or methylpyridine, preferably pyridine, and a catalytic amount of dimethyl sulfoxide. The mixture is allowed to react, typically at ambient temperature, but with heating, if necessary. After a substantial quantity of the compound of Formula I has formed or a substantial quantity of the chlorosulfonyl compound of Formula II has been consumed, the desired product is recovered, typically removing the solvent by evaporation, adding water, and removing the liquids from the solid that forms by filtration or centrifugation. The product recovered can be purified, if desired, by extracting with an immiscible organic solvent, such as methylene chloride, and with water. Alternatively, the desired compounds of Formula I can be purified by recrystallization and by other commonly used methods.

Approximately equimolar quantities of the compounds of Formulas II and III are generally used in the preparation of compounds of Formula I although a substantial excess of one or the other may be employed. The pyridine or methylpyridine compound is generally employed in an amount of from at least 1 to about 5 moles per mole of compound of Formula II. Dimethyl sulfoxide is typically used in less than an equimolar amount; amounts over about 0.3 mole per mole of compound of Formula II are usually deleterious. Acetonitrile is often the preferred solvent.

It is sometimes advantageous to prepare the compounds of Formula I by condensing a chlorosulfonyl compound of Formula II with an N-trialkylsilyl derivative of a substituted aminopyridine compound. The method employed is analogous to that described in U.S. Pat. No. 4,910,306 for N-trialkylsilylanilines. The reaction conditions required are essentially the same as those described hereinabove for the condensation of a compound of Formula II with a substituted aminopyridine with the exception that the pyridine compound base may be omitted. The substituted N-trialkylsilylaminopyridine compounds employed can be prepared from the corresponding substituted aminopyridine compounds by treatment with a trialkylsilyl halide and a trialkylamine as described in U.S. Pat. No. 4,910,306 for aniline compounds. Sodium iodide is typically employed as a catalyst when the halide is chloride. The N-trialkylsilylaminopyridine compounds are typically prepared and used immediately and without purification.

Compounds of Formula I wherein V represents hydrogen and OR represents $(C_1-C_3)$alkoxy optionally monosubstituted with chloro or methoxy or 2,2,2-trifluoroethoxy can be made from the corresponding compounds related to those of Formula I wherein the moiety OR in the 5-position is replaced by chloro by treatment with an appropriate alkoxide reagent, such as sodium methoxide in methanol. The reaction conditions employed are similar to those used for the related exchange reactions of 2- and 4-chloropyrimidines. Non-aqueous media are preferred. Selective replacement of chlorine in the 5-position can readily be achieved as this chlorine is much more reactive than chlorine in the 7- and 8-positions (Y and/or Z represent Cl).

Compounds of Formula I wherein V represents COR', $CO_2R''$, or $CONR'''_2$ can be prepared from compounds of Formula I wherein V represents hydrogen by acylation with a compound of the formula ClCOR', $ClCO_2R''$, or $ClCONR'''_2$, respectively, using conventional procedures known in the art for the acylation of sulfonamides.

The 2-chlorosulfonyl[1,2,4]triazolo[1,5-c]pyrimidine compounds of Formula II and their analogs wherein the moiety OR is replaced by chloro can be prepared by the methods taught in U.S. Pat. No. 5,010,195.

The preparation of several substituted 3-aminopyridines, notably those wherein A represents chloro or fluoro, and B represents alkyl, alkoxy or alkylthio is described in the Examples. Other substituted 3-aminopyridines of interest as intermediates for the compounds of Formula I are known in the art or can be prepared by the general methods known in the art or provided herein.

While it is possible to utilize the [1,2,4]triazolo[1,5-c]pyrimidine-2-sulfonamide compounds of Formula I directly as herbicides, it is preferable to use them in mixtures containing an herbicidally effective amount of the compound along with at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with the compounds of Formula I or other composition ingredients. Such mixtures can be designed for application directly to weeds or their locus or can be concentrates or formulations which are normally diluted with additional carriers and adjuvants before application. They can be solids, such as, for example, dusts, granules, water dispersible granules, or wettable powders, or liquids, such as, for example, emulsifiable concentrates, solutions, emulsions or suspensions.

Suitable agricultural adjuvants and carriers that are useful in preparing the herbicidal mixtures of the invention are well known to those skilled in the art.

Liquid carriers that can be employed include water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methanol, ethanol, isopropanol, amyl alcohol, ethylene glycol, propylene glycol, glycerine, and the like. Water is generally the carrier of choice for the dilution of concentrates.

Suitable solid carriers include talc, pyrophyllite clay, silica, attapulgus clay, kieselguhr, chalk, diatomaceous earth, lime, calcium carbonate, bentonite clay, Fuller's earth, cotton seed hulls, wheat flour, soybean flour, pumice, wood flour, walnut shell flour, lignin, and the like.

It is frequently desirable to incorporate one or more surface-active agents into the compositions of the present invention. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Typical surface active agents include salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalenesulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; and salts of mono and dialkyl phosphate esters.

Other adjuvants commonly utilized in agricultural compositions include antifoam agents, compatibilizing agents, sequestering agents, neutralizing agents and buffers, corrosion inhibitors, dyes, odorants, penetration aids, spreading agents, sticking agents, dispersing agents, thickening agents, freeze point depressants, antimicrobial agents, and the like. The compositions can also contain other compatible components, for example, other herbicides, plant growth regulants, fungicides, insecticides, and the like and can be formulated with liquid fertilizers or solid, particulate fertilizer carriers such as ammonium nitrate, urea and the like.

The concentration of the active ingredients in the herbicidal compositions of this invention is generally from about 0.001 to about 98 percent by weight. Concentrations from about 0.01 to about 90 percent by weight are often employed. In compositions designed to be employed as concentrates, the active ingredient is generally present in a concentration from about 5 to about 98 weight percent, preferably about 10 to about 90 weight percent. Such compositions are typically diluted with an inert carrier, such as water, before application. The diluted compositions usually applied to weeds or the locus of weeds generally contain about 0.001 to about 5 weight percent active ingredient and preferably contain about 0.01 to about 0.5 percent.

The present compositions can be applied to weeds or their locus by the use of conventional ground or aerial dusters, sprayers, and granule applicators, by addition to irrigation water, and by other conventional means known to those skilled in the art.

The compounds of Formula I have been found to be useful preemergence and postemergence herbicides. They can be employed at non-selective (higher) rates of application to control essentially all of the vegetation in an area or, in some cases, at selective (lower) rates of application for the selective control of undesirable vegetation in grass crops, such as corn, wheat, barley, and rice as well as in broadleaf crops, such as soybeans and cotton. While each of the N-pyridinyl [1,2,4]triazolo[1,5-a]pyrimidine-2-sulfonamide compounds encompassed by Formula I is within the scope of the invention, the degree of herbicidal activity, the crop selectivity, and the spectrum of weed control obtained varies depending upon the substituents present.

The term herbicide is used herein to mean an active ingredient which controls or adversely modifies the growth of plants. An herbicidally effective or vegetation controlling amount is an amount of active ingredient which causes an adversely modifying effect and includes deviations from natural development, killing, regulation, desiccation, retardation, and the like. The terms plants and vegetation are meant to include germinant seeds, emerging seedlings and established vegetation.

Herbicidal activity is exhibited by the compounds of the present invention when they are applied directly to the plant or to the locus of the plant at any stage of growth or before emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote selective herbicidal action. Generally, it is preferred to apply the compounds of Formula I postemergence to relatively immature plants to achieve the maximum control of broadleaf weeds.

Application rates of about 0.001 to about 1 Kg/Ha are generally employed in postemergence operations; for preemergence applications, rates of about 0.01 to about 10 Kg/Ha are generally employed. The higher rates designated generally give non-selective control of a broad variety of undesirable vegetation. The lower rates typically give selective control and, by judicious election, can be employed in the locus of crops.

EXAMPLES

The following Examples are presented to illustrate the various aspects of this invention and should not be construed as limitations to the claims.

1. Preparation of 3-Amino-2-fluoro-4-methylpyridine

To a solution of 10.1 g (grams) (65 mmol (millimole)) of 2-fluoro-4-methyl-3-nitropyridine in 200 mL (milliliter) of ethyl acetate was added 25 g (0.40 mol) of acetic acid and 0.8 g of 5 percent palladium on carbon catalyst. This mixture was shaken under 50 psig (pounds per square inch gauge, 2400 kiloPascals) pressure of hydrogen for 18 hours, was filtered, and was concentrated by evaporation under reduced pressure to obtain an oil. This oil was partitioned between dilute aqueous sodium bicarbonate and ether. The organic phase was separated, dried over magnesium sulfate, and filtered. The filtrate was concentrated by evaporation under reduced pressure and the residue was purified by column chromatography to obtain 7.2 g (88 percent of theory) of the title compound as a colorless solid melting at 63°–64° C.

Elemental Analysis $C_6H_7FN_2$ Calc.: %C, 57.1; %H, 5.59; %N, 22.2 Found: %C, 57.2; %H, 5.73; %N, 22.1 $^1$H NMR (nuclear magnetic resonance spectrum (200 megahertz)) $CDCl_3$: 7.4 (d, 1H, J=5.0); 6.8 (d, 1H, J=5.0); 3.7 (br, 2H); 2.1 (s, 3H); 13C NMR $CDCl_3$: 152.6 (d, J=229); 134.1 (d, J=8.6); 133.8 (d, J=14.5); 128.1 (d, J=27.1); 123.3, 16.4 (d, J=4.1).

3-Amino-2-fluoro-5-methylpyridine was prepared analogously from 2-fluoro-5-methyl-3-nitropyridine. This compound was obtained in 89 percent yield as white solid melting at 27°–28.5° C.

Elemental Analysis $C_6H_7FN_2$ Calc.: %C, 57.1; %H, 5.59; %N, 22.2 Found: %C, 56.9, %H, 5.65; %N, 22.6 $^1$H NMR $CDCl_3$: 7.2 (d, 1H); 6.8 (d, 1H); 3.7 (br, 2H); 2.1 (s, 3H); $^{13}$C NMR $CDCl_3$: 151.8 (d, J=229); 134.5 (d, J=12.6); 132.2 (d, J=3.9); 129.9 (d, J=28.7); 125.8 (d, J=5.3), 17.8.

2. Preparation Of 3-Amino-2-chloro-4-methoxypyridine

To a solution of 6.4 g (51 mmol) of 3-amino-4-methoxypyridine in 30 mL of 37 percent aqueous hydrochloric acid was slowly added 7.8 g of 30 percent aqueous hydrogen peroxide at room temperature with stirring. After 30 min this solution was slowly poured into 300 mL of saturated aqueous sodium bicarbonate and the resulting mixture was extracted with ether (3×200mL). The ethereal extracts were combined, dried over magnesium sulfate, and filtered, The filtrate was concentrated by evaporation under reduced pressure to obtain a light brown solid. This solid was purified by column chromatography (17:83 acetone:hexane) to obtain 6.54 g (81 percent of theory) of the title compound as colorless needles melting at 86°–87° C.

Elemental Analysis $C_6H_7ClN_2O$ Calc.: %C, 45.4; %H, 4.45; %N, 17.7 Found: %C, 45.4; %H, 4.65; %N, 17.8 $^1$H NMR $CDCl_3$: 7.7 (d, 1H, J=5.4), 6.6 (d, 1H, J=5.4), 4.0 (br, 2H), 3.8 (s, 3H); $^{13}$C NMR $CDCl_3$: 153.3, 138.5, 135.6, 129.9, 105.2, 55.9.

3-Amino-2-chloro-4-ethoxypyridine was prepared from 3-amino-4-ethoxypyridine in an analogous procedure and was obtained as a white solid melting at 72°–73° C.

Elemental Analysis $C_7H_9ClN_2O$ Calc.: %C, 48.7; %H, 5.26; %N, 16.2 Found: %C, 48.9; %H, 4.98; %N, 16.5. $^1$H NMR $CDCl_3$: 7.7 (d, 1H, J=5.4), 6.6 (d, 1H, J=5.4), 4.1 (q, 2H, J=7.0), 4.0 (br, 2H), 1.5 (t, 3H, J=7.0).

3-Amino-2-chloro-4-propoxypyridine was prepared from 3-amino-4-propoxypyridine in an analogous procedure and was obtained as a white solid melting at 46°–47° C.

Elemental Analysis $C_8H_{11}ClN_2O$ Calc.: %C, 51.5; %H, 5.94; %N, 15.0 Found: %C, 51.8;o%H, 5.97; %N, 15.2 $^1$H NMR $CDCl_3$: 7.7 (d, 1H, J=5.4), 6.6 (d, 1H, J=5.4), 4.1 (br, 2H), 4.0 (t, 2H, J=6.5), 1.84 (m, 2H), 1.0 (t, 3H, J=7.4).

3-Amino-2-chloro-4-(1-methylethoxy) pyridine was prepared from 3-amino-4-(1-methylethoxy)pyridine in an analogous procedure and was obtained as an amber oil.

Elemental Analysis $C_8H_{11}ClN_2O$ Calc.: %C, 51.5; %H, 5.94; %N, 15.0 Found: %C, 51.1; %H, 5.87; %N, 15.4 $^1$H NMR $CDCl_3$: 7.7 (d, 1H, J=5.5), 6.6 (d, 1H, J=5.4), 4.6 (m, 1H, J=6.0), 4.0 (br, 2H), 1.34 (d, 6H, J=6.0).

3. Preperation of 3-Amino-2-ethylthio-4-methylpyridine

2-Ethylthio-4-methyl-3-nitropyridine (10.0 g, 50.4 mmol) was added slowly with stirring to a solution of 57 g (0.25 mole) of stannous chloride in 250 mL of concentrated aqueous hydrochloric acid. An exothermic reaction took place. The solution was held at 70° C. for 30 min, cooled, and then poured slowly into saturated aqueous sodium bicarbonate solution. The resulting mixture was extracted with ether and the extract was dried over magnesium sulfate, filtered, and concentrated by evaporation under reduced pressure to obtain 5.8 g (68 percent of theory) of a light yellow oil that solidified upon standing. This solid was recrystallized from hexane to obtain 3.2 g of the title compound as a white solid melting at 37°–38° C.

Elemental Analysis $C_8H_{12}N_2S$ Calc.: %C, 57.1; %H, 7.19; %N, 16.7; %S, 19.1 Found: %C, 57.3; %H, 6.88; %N, 16.8; %S, 19.0 $^1$H NMR CDCl$_3$: 7.8 (d, 1H, J=4.8), 6.7 (d, 1H, J=4.8), 3.8 (br, 2H), 3.2 (q, 2H, J=7.4), 2.1 (s, 3H), 1.3 (t, 3H, J=7.4). $^{13}$C NMR CDCl$_3$: 142.2, 139.5, 139.3, 128.9, 122.4, 25.4, 17.0, 15.0.

4. Preparation of Methyl 3-Amino-2-chloroisonicotinate

A mixture of 18 g (118 mmol) of methyl 3-aminoisonicotinate and 12 g (60 mmol) of 1,3-dichloro-5,5-dimethylhydantoin in 1500 mL of tetrachloroethylene was warmed slowly to 80° C. with stirring and held there for 3 hours. The solution was then cooled, filtered, washed with dilute aqueous sodium bicarbonate, dried over magnesium sulfate, filtered, and concentrated by evaporation under reduced pressure to obtain a dark oil. This oil was purified by careful column chromatography to give 6.7 g (30 percent of theory) of the title compound as a colorless solid melting at 91°–92° C.

Elemental Analysis $C_7H_7ClN_2O_2$ Calc.: %C, 45.1; %H, 3.78; %N, 15.0 Found: %C, 45.2; %H, 3.94; %N, 15.1 $^1$H NMR CDCl$_3$: 7.7 (d, 1H, J=5.1); 7.6 (d, 1H, J=5.1); 6.2 (br, 2H); 3.9 (s, 3H); $^{13}$C NMR CDCl$_3$: 166.7, 141.9, 139.0, 134.7, 122.8, 116.5, 52.3.

5. Preparation of 3-Amino-4-ethyl-2-fluoropyridine

Trimethylsilyl chloride (2.2 g, (0.18 mmol) and sodium iodide (2.7 g, 0.18 mmol) were added to a solution of 3.6 g (0.15 mmol) of [-butyl N-(4-ethyl-2-fluoro-3-pyridyl)carbamate in 50 mL of dry acetonitrile with stirring at ambient temperature. After 2 hours the mixture was poured into ether and and the resulting solution was washed with dilute aqueous sodium bisulfite, dried over magnesium sulfate, and filtered. The filtrate was concentrated by evaporation under reduced pressure to obtain an oil. This oil was purified by column chromatography to obtain 1.6 g (76 percent of theory) of the title compound as a gold oil.

Elemental Analysis $C_7H_9FN_2$ Calc.: %C, 60.0; %H, 6.47; %N, 20.0 Found: %C, 59.8; %H, 6.66; %N, 20.2 $^1$H NMR CDCl$_3$: 7.4 (d, 1H, J=5.0); 6.8 (d, 1H, J=5.0); 3.7 (br, 2H); 2.45 (q, 2H, J=7.5); 1.2 (t, 3H, J=7.5).

3-Amino-4-(1-methylethyl)-2-fluoropyridine was prepared in an analogous way from t-butyl N-(4-(1-methylethyl) -2-fluoro-3-pyridyl)carbamate. This compound was obtained in 92 percent yield as a gold oil.

Elemental Analysis $C_8H_{11}FN_2$ Calc.: %C, 62.3; %H, 7.19; %N, 12.3 Found: %C, 62.5; %H, 7.24; %N, 12.6. $^1$H NHR CDCl$_3$: 7.4 (d, 1H, J=5.2); 6.8 (d, 1H, J=5.1); 3.8 (br, 2H); 2.87 (m, 1H); 1.2 (d, 6H, J=6.8).

6. Preparation of t-Butyl N-(4-Ethyl-2-fluoro-3-pyridyl)carbamate

A solution of lithium, diisopropylamine (LDA) was prepared from 19.3 mL (137 mmol) of diisopropylamine and 55 mL (137 mmo) of 2.5M n-butyllithium in hexane in 50 mL of dry tetrahydrofuran at −20° C. A solution of 14.4 g (62.5 mmol) of t-butyl N-(4-methyl-2-fluoro-3-pyridyl)carbamate in 80 mL of dry tetrahydrofuran was added dropwise with stirring at a rate slow enough to maintain the temperature below −60° C. After a 30 min reaction period, 27 g (190 mmol) of methyl iodide was added and the solution was allowed to warm to −10° C. The resulting mixture was diluted with 100 mL of aqueous ammonium chloride and 200 mL of ether and the phases were separated. The aqueous phase was washed with ether (3×100 mL). The organic phase and ether washes were combined, dried over magnesium sulfate, and filtered. The filtrate was concentrated by evaporation under reduced pressure to obtain a gold oil. This oil was purified by column chromatography to obtain 11.4 g (76 percent of theory) of the title compound as a white solid melting at 84°–86° C. $^1$H NMR CDCl$_3$: 7.7 (d, 1H, J=5.08); 6.8 (d, 1H, J=5.08); 6.1 (br, 1H); 2.45 (q, 2H, J=7.6); 1.2 (s, 9H); 1.0 3H, J=7.6).

t-Butyl N- (4-(1-methylethyl)-2-fluoro-3-pyridyl )carbamate was prepared analogously from t-butyl N-(4-ethyl-2-fluoro-3-pyridyl)carbamate. This compound was obtained in 69 percent yield as a colorless solid melting at 60°–62° C.

Elemental Analysis $C_{13}H_{19}FN_2O_2$ Calc.: %C, 61.4; %H, 7.53; %N, 11.0 Found: %C, 61.6; %H, 7.78; %N, 11.3. $^1$H NMR CDCl$_3$: 7.9 (d, 1H, J=5.4); 7.0 (d, 1H, J=5.4); 6.0 (br, 1H); 3.2 (m, 1H); 1.4 (s, 9H); 1.2 (d, 6H, J=5.2).

7. Preparation of 3-Amino-2,4,5-trichloropyridine

Thirty percent aqueous hydrogen peroxide (3.0 g, 26 mmole) was added dropwise with stirring at 15° C. to a solution of 8.0 g (49 mmol) of 3-amino-4,5-dichloropyridine in 450 mL of 37 percent aqueous hydrochloric acid. After 30 min another 2.6 g (23 mmol) of 30 percent aqueous hydrogen peroxide was added and the solution was allowed to slowly warm to room temperature. The resulting mixture was diluted with water, neutralized with sodium carbonate, and extracted with ether. The ethereal extract was dried over magnesium sulfate and filtered. The filtrate was concentrated by evaporation under reduced pressure to obtain a viscous oil. This oil was partially purified by column chromatography to obtain 2.5 g (26 percent of theory) of the title compound, a white solid melting at 88°–90° C., and 5.3 g of a mixture of the title compound and 3-amino-2,4,5,6-tetrachloropyridine.

Elemental Analysis $C_5H_3Cl_3N_2$ Calc.: %C, 30.4; %H, 1.53; %N, 14.2 Found: %C, 30.5; %H, 1.47; %N, 14.1. $^1$H NMR CDCl$_3$: 7.7 (s, 1H); 4.6 (br, 2H).

8. Preparation of N-(2-Chloro-4-methoxy-3-pyridinyl)-7-fluoro-5-methoxy[1,2,4]triazolo[5-c]pyrimidine-2-sulfonamide To a solution of 5.4 g (33.8 mmol) of 3-amino-2-chloro-4-methoxypyridine and 3.0 g (11.3 mmol) of 2-chlorosulfonyl-7-fluoro-5-methoxy[1,2,4]triazolo[1,5-c]pyrimidine in 20 mL of dry acetonitrile was added with stirring 0.91 mL (11.3 mmol) of dry pyridine and 0.16 mL (2.3 mmol) of dry dimethyl sulfoxide (DMSO). After 2 hours the resulting slurry was poured into a mixture of 200 mL of water and 800 mL of dichloromethane and the resulting mixture was stirred for 1 hour. The organic phase was recovered, dried over magnesium sulfate, filtered, and concentrated by evaporation under reduced pressure. The residue remaining was purified by flash column chromatography to obtain 1.6 g (38 percent of theory) of the title compound as a white solid melting at 187°–188° C.

Elemental Analysis $C_{12}H_{10}ClFN_6O_4S$ Calc.: %C, 37.1; %H, 2.59; %N, 21.2; %S, 8.25 Found: %C, 37.3; %H, 2.46; %N, 21.5; %S, 8.22 $^1$H NMR DMSO-d$_6$: 10.7 (br, 1H), 8.2 (d, 1H, J=5.7), 7.4 (s, 1H), 7.1 (d, 1H, J=5.7), 4.2 (s, 3H), 3.4 (s, 3H).

8. Preparation of N-(2-chloro-4-methoxy-3-pyridyl)-5,7-dimethoxy[1,2,4]triazolo[1,5-c]pyrimidine-2-sulfonamide To a solution of 0.60 g (1.5 mmol) of N-(2-chloro-4-methoxy-3-pyridinyl)-7-fluoro-5-methoxy[1,2,4]triazolo[1, 5-c]pyrimidine-2-sulfonamide in 20 mL of dimethyl sulfoxide was added with stirring 0.24 g (3.4 mmol) of potassium methoxide in 2.4 mL of dry methanol. After 1 hour 5 mL of acetic acid was added and the solution taken up in 400 mL of dichloromethane. The resulting solution was washed with water (6×150 mL), dried over magnesium sulfate, filtered, and concentrated by evaporation under reduced pressure to obtain 270 mg (20 percent of theory) of the title compound as a white solid melting at 197°–199° C. with decomposition.

Elemental Analysis $C_{13}H_{13}ClN_6O_4S$ Calc.: %C, 39.0; %H, 3.27; %N, 21.0 Found: %C, 39.0; %H, 3.40; %N, 20.9 $^1$H NMR DMSO-$d_6$: 10.6 (br, 1H); 8.2 (d, 1H, J=5.7); 7.1 (d, 1H, J=5.7); 6.7 (s, 1H); 4.2 (s, 3H); 3.9 (s, 3H); 3.4 (s, 3H).

9. Preparation of N-(4-Ethoxy-3-pyridinyl) -5-methoxy-7-methyl[1,2,4,]trriazolo[1,5-c]pyrimidine-2-sulfonamide 2-Chlorosulfonyl-5-methoxy-7-methyl[1,2,4]triazolo[1,5-c]pyrimidine (1.5 g, 5.7 mmol) was added to a solution of 0.8 g (5.7 mmol) of 3-amino-4-ethoxypyridine in 30 mL of dry pyridine in portions over 10 minutes with stirring. After 16 hours the reaction mixture was poured into 400 mL of dichloromethane. The resulting mixture was washed with 150 mL of water, dried over magnesium sulfate, and filtered. The filtrate was combined with 5 g of silica gel and the mixture was concentrated by evaporation under reduced pressure. The resulting silica plug was placed onto a 200 g silica gel column and eluted with dichloromethane containing increasing amount of ethanol. The product fractions were combined and concentrated by evaporation under reduced pressure and the solid obtained was dried to obtain 0.75 g (36 percent of theory) of the title compound as a white solid melting at 184°–186° C.

Elemental Analysis $C_{14}H_{16}N_6O_4S$ Calc.: %C, 46.2; %H, 4.43; %N, 23.1; %S, 8.08 Found: %C, 46.5; %H, 4.37; %N, 22.8; %S, 7.98 $^1$H NMR (DMSO-$d_6$): 10.5 (br, 1H); 8.3 (s, 1H); 8.26 (d, 1H, J=5.6); 7.4 (s, 1H); 7.0 (d, 1H, J=5.6); 4.2 (s, 3H); 3.9 (q, 2H, J=7.0); 2.5 (s, 1H); 1.0 (t, 3H, J=7.0).

10. Evaluation of Postemergence Herbicidal Activity

Seeds of the desired test plant species were planted in Grace-Sierra MetroMix® 306 planting mixture, which typically has a pH of 6.0 to 6.8 and an organic matter content of about 30 percent, in plastic pots with a surface area of 64 square centimeters. When required to ensure good germination and healthy plants, a fungicide treatment and/or other chemical or physical treatment was applied. The plants were grown for 7–21 days in a greenhouse with an approximately 15 hr photoperiod which was maintained at about 23°–29° C. during the day and 22°–28° C. during the night. Nutrients and water were added on a regular basis and supplemental lighting was provided with overhead metal halide 1000 Watt lamps as necessary. The plants were employed for testing when they reached the first or second true leaf stage.

A weighed amount, determined by the highest rate to be tested, of each test compound was placed in a 20 mL glass vial and was dissolved in 4 mL of a 97:3 v/v (volume/volume) mixture of acetone and dimethyl sulfoxide to obtain concentrated stock solutions. If the test compound did not dissolve readily, the mixture was warmed and/or sonicated. The concentrated stock solutions obtained were diluted with an aqueous mixture containing acetone, water, isopropyl alcohol, dimethyl sulfoxide, Atplus 411F crop oil concentrate, and Triton X-155 surfactant in a 48.5:39:10:1.5:1.0:0.02 v/v ratio to obtain spray solutions of known concentration. The solutions containing the highest concentration to be tested were prepared by diluting 2 mL aliquots of the stock solution with 13 mL of the mixture and lower concentrations were prepared by dilution of appropriate smaller portions of the stock solution. Approximately 1.5 mL aliquots of each solution of known concentration were sprayed evenly onto each of the test plant pots using a DeVilbiss atomizer driven by compressed air pressure of 2 to 4 psi (140 to 280 kiloPascals) to obtain thorough coverage of each plant. Control plants were sprayed in the same manner with the aqueous mixture. In this test an application rate of 1 ppm results in the application of approximately 1 g/Ha.

The treated plants and control plants were placed in a greenhouse as described above and watered by sub-irrigation to prevent wash-off of the test compounds. After 2 weeks the condition of the test plants as compared with that of the untreated plants was determined visually and scored on a scale of 0 to 100 percent where 0 corresponds to no injury and 100 corresponds to complete kill. Some of the compounds tested, application rates employed, plant species tested, and results are given in Table 2.

TABLE 2

| | | | | | | POSTEMERGENCE HERBICIDAL ACTIVITY | | | | |
|---|---|---|---|---|---|---|---|---|---|---|
| Cpd. No. | Rate, ppm | Cockle-bur | Jimson-weed | Morning-glory | Velvet-leaf | Veronica | Wild Buck-wheat | Black-grass | Giant foxtail | Johnson-grass |
| 1 | 1000 | 15 | 85 | 15 | 65 | — | 30 | 55 | 0 | 15 |
| 2 | 250 | 55 | 40 | 70 | 40 | 50 | 70 | 35 | 0 | 0 |
| 3 | 125 | 250 | 85 | 90 | 100 | 89 | 85 | 85 | 90 | 70 |
| 4 | 250 | 100 | 100 | 85 | 88 | 80 | 88 | 75 | 30 | 60 |
| 5 | 250 | 90 | 80 | 85 | 95 | 90 | 85 | 80 | 85 | 75 |
| 6 | 2000 | 80 | 85 | 0 | 85 | 30 | 80 | 50 | 60 | 15 |
| 7 | 1000 | 80 | 50 | 85 | 85 | 80 | 88 | 50 | 80 | 20 |
| 8 | 31.3 | 90 | — | 95 | 98 | 100 | 85 | 80 | 78 | 70 |
| 9 | 250 | 90 | — | 75 | 85 | 100 | 90 | 80 | 80 | 78 |
| 10 | 125 | 90 | 80 | 70 | 85 | 70 | 75 | 80 | 40 | 90 |
| 11 | 2000 | 75 | 80 | 75 | 70 | 98 | 70 | 80 | 78 | 75 |
| 12 | 1000 | 80 | 90 | 90 | 75 | 90 | 80 | 98 | 75 | 90 |
| 13 | 7.81 | 100 | 90 | 50 | 80 | 98 | 90 | 70 | 70 | 80 |
| 14 | 15.6 | 99 | 83 | 100 | 100 | 0 | 85 | 75 | 20 | 95 |
| 15 | 7.81 | 90 | 88 | 85 | 75 | 70 | 75 | 60 | 60 | 85 |
| 16 | 15.6 | 100 | — | 90 | 90 | 70 | 85 | 70 | 80 | 90 |
| 17 | 62.5 | 85 | 90 | 85 | 95 | 70 | 90 | 70 | 30 | 60 |
| 18 | 15.6 | 80 | — | 80 | 80 | 60 | 80 | 75 | 50 | 75 |
| 19 | 7.81 | 85 | — | 100 | 80 | 40 | 80 | 60 | 50 | 78 |
| 20 | 7.81 | 98 | — | 95 | 80 | 0 | 80 | 40 | 0 | 75 |

TABLE 2-continued

POSTEMERGENCE HERBICIDAL ACTIVITY

| Cpd. No. | Rate, ppm | Cocklebur | Jimsonweed | Morningglory | Velvetleaf | Veronica | Wild Buckwheat | Blackgrass | Giant foxtail | Johnsongrass |
|---|---|---|---|---|---|---|---|---|---|---|
| 21 | 7.81 | 90 | 70 | 70 | 98 | 70 | 70 | 60 | 20 | 85 |
| 22 | 15.6 | 85 | 85 | 75 | 75 | 45 | 80 | 40 | 40 | 60 |
| 23 | 15.6 | 98 | 80 | 80 | 90 | 80 | 90 | 80 | 35 | — |
| 24 | 15.6 | 100 | 80 | 100 | 50 | 70 | 90 | 70 | 80 | 90 |
| 25 | 31.3 | 100 | 95 | 85 | 100 | 70 | 100 | 78 | 60 | 90 |
| 26 | 15.6 | 98 | 100 | 85 | 90 | 20 | 100 | 70 | 40 | 0 |
| 27 | 31.3 | 80 | 80 | 80 | 80 | 0 | 80 | 0 | 0 | 45 |
| 28 | 500 | 15 | 80 | 70 | 80 | 70 | 70 | 85 | 80 | 90 |
| 29 | 15.6 | 100 | 93 | 75 | 65 | 80 | 95 | 45 | 40 | 83 |
| 30 | 31.3 | 75 | 80 | 70 | 98 | 60 | 75 | 95 | 10 | 100 |
| 31 | 500 | 80 | 80 | 70 | 80 | 90 | 75 | 85 | 75 | 85 |
| 32 | 125 | 90 | 80 | 70 | 85 | 40 | 80 | 80 | 45 | 75 |
| 33 | 125 | 70 | 80 | 80 | 80 | 85 | 85 | 75 | 30 | 40 |
| 34 | 15.6 | 99 | 80 | 80 | 80 | 100 | 98 | 20 | 45 | 80 |
| 35 | 31.3 | 90 | 85 | 88 | 85 | 88 | 85 | 90 | 85 | 88 |
| 36 | 125 | 70 | 88 | 90 | 85 | 100 | 86 | 90 | 85 | 84 |
| 37 | 62.5 | 85 | 90 | 90 | 89 | 100 | 80 | 89 | 85 | 85 |
| 38 | 15.6 | 88 | 80 | 85 | 88 | 75 | 88 | 75 | 80 | 80 |
| 39 | 250 | 75 | 70 | 85 | 95 | 95 | 95 | 90 | 90 | 90 |
| 40 | 7.81 | 83 | 95 | 70 | 83 | 100 | 75 | 60 | 40 | 75 |
| 41 | 31.3 | 70 | 80 | 85 | 93 | 70 | 93 | 80 | 20 | 83 |
| 42 | 31.3 | 100 | 70 | 75 | 80 | 100 | 100 | 70 | 70 | 85 |
| 43 | 125 | 85 | 80 | 88 | 100 | 75 | 85 | 50 | 50 | 85 |
| 44 | 500 | 50 | 75 | 85 | 85 | 50 | 85 | 70 | 20 | 75 |
| 45 | 31.3 | — | — | 90 | 88 | 70 | 80 | 50 | 85 | 90 |
| 46 | 31.3 | — | — | 88 | 88 | 88 | 88 | 75 | 70 | 95 |
| 47 | 62.5 | 75 | 80 | 85 | 80 | 80 | 78 | 80 | 65 | 80 |
| 48 | 7.81 | 90 | 0 | 85 | 80 | 80 | 80 | 70 | 70 | 90 |
| 49 | 15.6 | 100 | 88 | 88 | 80 | 80 | 80 | 40 | 40 | 85 |
| 50 | 15.6 | 100 | 88 | 90 | 85 | 70 | 84 | 35 | 30 | 85 |
| 51 | 31.3 | 90 | 90 | 88 | 88 | 90 | 80 | 88 | 90 | 80 |
| 52 | 15.6 | 90 | — | 85 | 70 | 75 | 85 | 55 | 70 | 85 |
| 53 | 15.6 | 90 | — | 88 | 85 | 88 | 88 | 55 | 70 | 100 |
| 54 | 500 | 90 | — | 90 | 85 | 85 | 90 | 70 | 70 | 85 |
| 55 | 250 | 95 | 98 | 90 | 80 | 80 | 90 | 70 | 40 | 60 |
| 56 | 62.5 | 90 | 80 | 80 | 75 | 80 | 75 | 65 | 20 | 70 |
| 57 | 31.3 | 20 | 80 | 40 | 85 | 70 | 75 | 90 | 70 | 85 |
| 58 | 500 | 60 | 80 | 60 | 80 | 95 | 80 | 80 | 80 | 80 |
| 59 | 62.5 | 40 | 80 | 60 | 80 | 90 | 80 | 75 | 70 | 90 |
| 60 | 500 | 85 | 75 | 80 | 88 | 90 | 70 | 80 | 90 | 75 |
| 61 | 62.5 | 60 | 85 | 80 | 85 | 95 | 90 | 90 | 90 | 90 |
| 63 | 15.6 | 70 | 70 | 80 | 90 | 85 | 85 | 90 | 40 | 88 |
| 64 | 500 | 100 | 95 | 75 | 85 | 85 | 85 | 65 | 50 | 85 |
| 65 | 250 | 100 | 95 | 90 | 80 | 80 | 75 | 60 | 60 | 60 |
| 66 | 250 | 100 | 90 | 85 | 75 | 98 | 85 | 60 | 60 | 30 |
| 67 | 1000 | 99 | 70 | 45 | 40 | 85 | 75 | 45 | 10 | 60 |
| 68 | 1000 | 100 | 80 | 90 | 75 | 83 | 93 | 70 | 45 | 80 |
| 69 | 62.5 | 97 | 55 | 70 | 95 | 99 | 90 | 45 | 70 | 75 |
| 70 | 1000 | 97 | 83 | 95 | 75 | 70 | 70 | 80 | 65 | 20 |
| 71 | 500 | 100 | 90 | 95 | 85 | 83 | 50 | 50 | 65 | 0 |
| 72 | 62.5 | 100 | 80 | 100 | 90 | 90 | 85 | 80 | 70 | 100 |
| 73 | 31.3 | 98 | 75 | 80 | 75 | 90 | 80 | 75 | 60 | 90 |
| 74 | 1000 | 85 | 75 | 80 | 80 | 85 | 83 | 75 | 70 | 99 |
| 75 | 250 | 100 | 75 | 75 | 90 | 90 | 80 | 85 | 100 | 75 |
| 76 | 1000 | 80 | 75 | 85 | 50 | 40 | 70 | 70 | 75 | 60 |
| 77 | 500 | 98 | — | 75 | 75 | — | 65 | 70 | 75 | — |
| 78 | 62.5 | 100 | — | 100 | 100 | — | 80 | 90 | 80 | — |
| 79 | 31.3 | 100 | — | 88 | 85 | — | 87 | 70 | 75 | — |
| 80 | 15.6 | 100 | — | 85 | 85 | — | 88 | 90 | 85 | — |
| 81 | 1.95 | 88 | — | 85 | 85 | — | 80 | 85 | 70 | — |
| 82 | 15.6 | 90 | — | 90 | 85 | — | 80 | 85 | 30 | — |
| 83 | 62.5 | 90 | — | 80 | — | — | — | 75 | 85 | — |
| 84 | 500 | 78 | — | 75 | 60 | — | 50 | 75 | 85 | — |
| 85 | 250 | 90 | — | 80 | 70 | — | 78 | 80 | 80 | — |
| 86 | 500 | 88 | — | 90 | 70 | — | 70 | 70 | 75 | — |
| 87 | 62.5 | 100 | — | 85 | 80 | — | 80 | 60 | 70 | — |
| 88 | 62.5 | 90 | — | 100 | 75 | — | 85 | 35 | 40 | — |
| 89 | 15.6 | 100 | — | 90 | 90 | — | 75 | 40 | 40 | — |
| 90 | 250 | 100 | — | 90 | 90 | — | 88 | 90 | 80 | — |
| 91 | 125 | 100 | — | 85 | 88 | — | 80 | 85 | 75 | — |
| 92 | 125 | 100 | — | 78 | 90 | — | 85 | 85 | 50 | — |
| 93 | 31.3 | 95 | — | 85 | 85 | — | 80 | 80 | 45 | — |
| 95 | 125 | 100 | — | 80 | 75 | — | 70 | 70 | 70 | — |

TABLE 2-continued

POSTEMERGENCE HERBICIDAL ACTIVITY

| Cpd. No. | Rate, ppm | Cockle-bur | Jimson-weed | Morning-glory | Velvet-leaf | Veronica | Wild Buck-wheat | Black-grass | Giant foxtail | Johnson-grass |
|---|---|---|---|---|---|---|---|---|---|---|
| 96 | 7.8 | 100 | — | 98 | 70 | — | 70 | 40 | 20 | — |
| 97 | 500 | 100 | — | 85 | 85 | — | 85 | 70 | 60 | — |
| 98 | 250 | 100 | — | 80 | 80 | — | 80 | 50 | 20 | — |
| 99 | 250 | 90 | — | 85 | 85 | — | 85 | 80 | 85 | — |
| 100 | 62.5 | 90 | — | 85 | 90 | — | 95 | 90 | 95 | — |
| 101 | 15.6 | 100 | — | 80 | 80 | — | 70 | 90 | 70 | — |
| 102 | 125 | 100 | — | 80 | 70 | — | 80 | 30 | 80 | — |
| 103 | 500 | 100 | — | 80 | 70 | — | 80 | 85 | 80 | — |
| 104 | 62.5 | 100 | — | 90 | 90 | — | 70 | 90 | 30 | — |
| 105 | 62.5 | 80 | — | 90 | 60 | — | 70 | 65 | 60 | — |
| 107 | 31.3 | 70 | — | 80 | 75 | — | 70 | 95 | 95 | — |
| 108 | 31.3 | 100 | — | 98 | 98 | — | 80 | 65 | 30 | — |

11. Evaluation of Preemergence Herbicidal Activity

Seeds of the desired test plant species were planted in a soil matrix prepared by mixing a loam soil which was composed of about 43 percent silt, 19 percent clay, and 38 percent sand and had a pH of about 8.1 and an organic matter content of about 1.5 percent and sand in a 70 to 30 ratio. The soil matrix was contained in plastic pots with a surface area of 161 square centimeters. When required to ensure good germination and healthy plants, a fungicide treatment and/or other chemical or physical treatment was applied.

A weighed amount, determined by the highest rate to be tested, of each test compound was placed in a 20 mL glass vial and was dissolved in 8 mL of a 97:3 v/v (volume/volume) mixture of acetone and dimethyl sulfoxide to obtain concentrated stock solutions. If the test compound did not dissolve readily, the mixture was warmed and/or sonicated. The stock solutions obtained were diluted with a 99.9:0.1 mixture of water and Tween® 155 surfactant to obtain application solutions of known concentration. The solutions containing the highest concentration to be tested were prepared by diluting 4 mL aliquots of the stock solution with 8.5 mL of the mixture and lower concentrations were prepared by dilution of appropriate smaller portions of the stock solution. A 2.5 mL aliquot of each solution of known concentration was sprayed evenly onto the soil of each seeded pot using a Cornwall 5.0 mL glass syringe fitted with a TeeJet TN-3 hollow cone nozzle to obtain thorough coverage of the soil in each pot. Control pots were sprayed in the same manner with the aqueous mixture. A highest application rate of 4.48 Kg/Ha is achieved when 50 mg of test compound is employed.

The treated pots and control pots were placed in a greenhouse with an approximately 15 hr photoperiod which was maintained at about 23°–29° C. during the day and 22°–28° C. during the night. Nutrients and water were added on a regular basis and supplemental lighting was provided with overhead metal halide 1000 Watt lamps as necessary. The water was added by top-irrigation. After 3 weeks the condition of the test plants that germinated and grew as compared with that of the untreated plants that germinated and grew was determined visually and scored on a scale of 0 to 100 percent where 0 corresponds to no injury and 100 corresponds to complete kill or no germination. Some of the compounds tested, application rates employed, plant species tested, and results are given in Table 3.

TABLE 3

PREEMERGENCE HERBICIDAL ACTIVITY

| Cpd. No. | Rate, Kg/Ha | Morning-glory | Pigweed | Velvet-leaf | Wild Buck-wheat | Black-grass | Barn-yard Grass | Giant foxtail | Johnson-grass |
|---|---|---|---|---|---|---|---|---|---|
| 2 | 1.12 | 40 | 50 | 75 | 60 | 70 | 60 | 50 | 50 |
| 3 | 0.56 | 85 | 80 | 80 | 80 | 70 | 90 | 95 | 20 |
| 4 | 1.12 | 90 | 100 | 85 | 98 | 10 | 95 | 75 | 75 |
| 5 | 2.24 | 60 | 75 | 85 | 85 | 25 | 98 | 98 | 20 |
| 8 | 0.56 | 50 | 90 | 80 | 90 | 90 | 90 | 98 | 50 |
| 9 | 1.12 | 80 | 95 | 85 | 90 | 80 | 98 | 98 | 90 |
| 10 | 1.12 | 85 | 90 | 95 | 90 | 98 | 95 | 75 | — |
| 11 | 4.48 | 50 | 100 | 98 | 30 | 100 | 100 | 60 | 100 |
| 13 | 0.035 | 90 | 100 | 95 | — | 90 | 65 | 90 | 90 |
| 14 | 0.14 | 80 | 98 | 95 | 90 | 85 | 95 | 80 | — |
| 15 | 0.14 | 90 | 85 | 90 | 90 | 85 | 90 | 90 | 90 |
| 16 | 0.018 | 40 | 100 | 90 | 100 | 80 | 90 | 80 | — |
| 17 | 0.035 | 80 | 98 | 95 | 50 | 70 | 90 | 20 | — |
| 18 | 0.035 | 80 | 95 | 80 | 50 | 90 | 95 | 30 | — |
| 19 | 0.018 | 80 | 90 | 90 | 80 | 50 | 80 | 60 | — |
| 20 | 0.035 | 90 | 90 | 80 | 80 | 80 | 95 | 50 | — |
| 21 | 0.018 | 80 | 98 | 80 | 70 | 60 | 95 | 60 | — |
| 22 | 0.035 | 90 | 85 | 95 | 80 | 70 | 85 | 20 | — |
| 23 | 0.14 | 80 | 90 | 95 | 90 | 30 | 0 | 60 | 60 |
| 24 | 0.070 | 90 | 100 | 70 | 90 | 90 | 98 | 100 | 90 |

TABLE 3-continued

PREEMERGENCE HERBICIDAL ACTIVITY

| Cpd. No. | Rate, Kg/Ha | Morning-glory | Pigweed | Velvet-leaf | Wild Buck-wheat | Black-grass | Barn-yard Grass | Giant foxtail | Johnson-grass |
|---|---|---|---|---|---|---|---|---|---|
| 25 | 0.070 | 60 | 100 | 80 | 75 | 60 | 98 | 20 | 85 |
| 26 | 0.035 | 90 | 100 | 85 | 95 | 90 | 90 | 60 | 80 |
| 27 | 0.035 | 60 | 100 | 95 | 90 | 95 | 98 | 80 | 80 |
| 28 | 0.056 | 50 | 98 | 98 | 80 | 98 | 98 | 98 | 75 |
| 29 | 0.070 | 80 | 90 | 80 | 85 | 75 | 100 | 75 | 90 |
| 30 | 0.14 | 95 | 90 | 95 | 85 | 98 | 98 | 50 | 98 |
| 31 | 1.12 | 50 | 75 | 50 | 30 | 75 | 75 | 50 | 75 |
| 32 | 0.56 | 98 | 98 | 85 | 90 | 98 | 98 | 50 | 98 |
| 33 | 0.28 | 90 | 95 | 80 | 95 | 75 | 60 | 40 | 80 |
| 34 | 0.070 | 75 | 100 | 90 | 90 | 50 | 50 | 70 | 80 |
| 35 | 0.070 | 80 | 95 | 85 | 80 | 100 | 70 | 90 | 90 |
| 36 | 0.28 | 85 | 60 | 85 | 90 | 100 | 98 | 90 | 90 |
| 37 | 0.018 | 80 | 80 | 75 | 90 | 90 | 98 | 80 | 85 |
| 38 | 0.28 | 90 | 98 | 95 | 98 | 90 | 85 | 95 | 98 |
| 39 | 0.035 | 40 | 90 | 85 | 98 | 80 | 90 | 85 | 90 |
| 40 | 0.018 | 90 | 100 | 90 | — | 40 | 60 | 75 | 90 |
| 41 | 0.28 | 90 | 100 | 98 | — | 85 | 90 | 95 | 90 |
| 42 | 0.035 | 90 | 100 | 95 | — | 50 | 40 | 60 | 90 |
| 43 | 0.56 | 90 | 30 | 75 | 90 | 95 | 98 | 60 | 90 |
| 45 | 0.035 | 70 | 98 | 80 | 88 | 40 | 70 | 85 | 85 |
| 46 | 0.28 | 40 | 90 | 60 | 70 | 0 | 60 | 65 | 85 |
| 47 | 0.14 | 40 | 90 | 80 | 87 | 95 | 75 | 80 | 80 |
| 48 | 0.009 | 60 | 95 | 70 | 75 | 80 | 90 | 70 | 90 |
| 49 | 0.070 | 90 | 98 | 85 | 95 | 75 | 90 | 78 | 90 |
| 50 | 0.14 | 90 | 98 | 85 | 95 | 65 | 98 | 65 | 90 |
| 51 | 0.070 | 88 | 90 | 90 | 85 | 95 | 80 | 85 | 88 |
| 52 | 0.035 | 90 | 90 | 75 | 90 | 65 | 80 | 70 | 90 |
| 53 | 0.009 | 90 | 85 | 85 | 88 | 85 | 90 | 75 | 88 |
| 54 | 0.14 | 90 | 85 | 85 | 90 | 60 | 70 | 45 | 80 |
| 55 | 0.56 | 90 | 90 | 65 | 90 | 70 | 65 | 30 | 80 |
| 56 | 0.28 | 85 | 80 | 75 | 80 | 40 | 40 | 30 | 65 |
| 57 | 0.56 | 75 | 80 | 85 | 50 | 80 | 55 | 80 | 90 |
| 58 | 1.12 | 65 | 95 | 80 | 55 | 95 | 70 | 75 | 90 |
| 59 | 0.14 | 75 | 90 | 90 | 90 | 75 | 70 | 90 | 90 |
| 60 | 1.12 | 100 | 90 | 65 | 70 | 98 | 80 | 65 | 80 |
| 61 | 0.14 | 90 | 98 | 88 | 90 | 10 | 70 | 90 | 80 |
| 63 | 0.14 | 70 | 90 | 85 | 90 | 95 | 95 | 80 | 95 |
| 64 | 1.12 | 80 | 80 | 60 | 80 | 98 | 60 | 75 | 95 |
| 65 | 0.56 | 80 | 60 | 70 | 50 | 99 | 80 | 80 | 90 |
| 66 | 0.56 | 90 | 70 | 60 | 70 | 90 | 90 | 90 | 70 |
| 67 | 0.28 | 20 | 70 | 30 | 65 | 90 | 70 | 30 | 80 |
| 68 | 0.28 | 65 | 80 | 50 | 85 | 100 | 90 | 80 | 90 |
| 69 | 0.070 | 85 | 90 | 75 | 90 | 60 | 70 | 70 | 75 |
| 70 | 1.12 | 30 | 50 | 40 | 20 | 30 | 85 | 95 | 50 |
| 71 | 2.24 | 75 | 90 | 50 | 40 | 50 | 90 | 70 | 60 |
| 72 | 0.070 | 50 | 90 | 50 | 60 | 50 | 50 | 60 | 90 |
| 73 | 0.035 | 70 | 70 | 70 | 80 | 85 | 95 | 90 | 90 |
| 74 | 1.12 | 60 | 90 | 50 | 50 | 50 | 70 | 50 | 90 |
| 75 | 0.56 | 80 | 95 | 80 | 90 | 80 | 85 | 95 | 50 |
| 77 | 0.28 | 40 | 50 | 50 | — | 70 | 70 | 90 | — |
| 78 | 0.070 | 85 | 95 | 95 | — | 95 | 98 | 90 | — |
| 79 | 0.28 | 85 | 75 | 90 | — | 85 | 85 | 95 | — |
| 80 | 0.070 | 80 | 85 | 98 | — | 98 | 20 | 95 | — |
| 81 | 0.070 | 90 | 90 | 90 | — | 95 | 80 | 85 | — |
| 82 | 0.28 | 95 | 50 | 80 | — | 100 | 95 | 60 | — |
| 83 | 0.28 | 90 | 80 | 70 | — | 85 | 95 | 60 | — |
| 84 | 2.24 | 85 | 90 | 65 | — | 90 | 65 | 70 | — |
| 85 | 1.12 | 75 | 50 | 75 | — | 80 | 75 | 60 | — |
| 87 | 0.070 | 80 | 60 | 85 | — | 80 | 95 | 85 | — |
| 88 | 0.14 | 80 | 80 | 90 | — | 80 | 95 | 80 | — |
| 89 | 0.14 | 85 | 75 | 85 | — | 85 | 90 | 80 | — |
| 90 | 0.070 | 90 | 90 | 95 | — | 95 | 85 | 70 | — |
| 91 | 0.070 | 85 | 85 | 90 | — | 95 | 90 | 95 | — |
| 92 | 0.56 | 75 | 80 | 90 | — | 95 | 95 | 75 | — |
| 93 | 0.14 | 85 | 75 | 90 | — | 98 | 95 | 25 | — |
| 94 | 0.28 | 60 | 40 | 25 | — | 70 | 75 | 70 | — |
| 97 | 1.12 | 90 | 85 | 70 | — | 60 | 70 | 50 | — |
| 98 | 1.12 | 78 | 90 | 85 | — | 65 | 80 | 75 | — |
| 101 | 0.035 | 85 | 80 | 85 | — | 85 | 85 | 75 | — |
| 102 | 0.28 | 35 | 70 | 80 | — | 90 | 95 | 80 | — |
| 103 | 0.28 | 35 | 65 | 80 | — | 85 | 85 | 60 | — |
| 104 | 0.070 | 85 | 80 | 95 | — | 95 | 75 | 50 | — |
| 105 | 0.14 | 90 | 90 | 85 | — | 90 | 70 | 75 | — |

TABLE 3-continued

| | | PREEMERGENCE HERBICIDAL ACTIVITY | | | | | | | |
|---|---|---|---|---|---|---|---|---|---|
| Cpd. No. | Rate, Kg/Ha | Morning-glory | Pigweed | Velvet-leaf | Wild Buck-wheat | Black-grass | Barn-yard Grass | Giant foxtail | Johnson-grass |
| 108 | 0.14 | 90 | 74 | 95 | — | 85 | 90 | 75 | —120 |

What is claimed is:

1. A 3-aminopyridine compound of the formula:

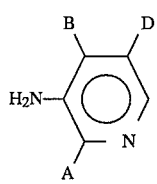

wherein A represents F, B represents $(C_1-C_4)$alkyl, and D represents H or wherein A represents F, Cl, or Br, B represents $(C_1-C_4)$alkoxy, and D represents H.

2. The compound according to claim 1: 3-amino-2-fluoro-4-methylpyridine.

3. A compound according to claim 1 which is a 3-amino-2-chloro-4-$(C_1-C_4)$alkoxypyridine.

* * * * *